(12) United States Patent
Tanaka et al.

(10) Patent No.: US 7,531,770 B2  
(45) Date of Patent: May 12, 2009

(54) METHOD FOR INSPECTING BOLT HEATER HOLE

(75) Inventors: Yoji Tanaka, Yokohama (JP); Shigeo Morimoto, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 11/672,790

(22) Filed: Feb. 8, 2007

(65) Prior Publication Data

US 2007/0181566 A1  Aug. 9, 2007

(30) Foreign Application Priority Data

Feb. 9, 2006 (JP) ............................. 2006-032624

(51) Int. Cl.  
*H05B 3/58* (2006.01)

(52) U.S. Cl. ...................................... 219/535; 219/205

(58) Field of Classification Search ................. 219/535, 219/205, 301, 456, 528, 549, 201, 545; 123/184.21, 123/198; 15/104.165  
See application file for complete search history.

(56) References Cited

U.S. PATENT DOCUMENTS 4,497,082 A * 2/1985 Kogasaka ............ 151/104.165

FOREIGN PATENT DOCUMENTS

JP  9-196863  7/1997

* cited by examiner

*Primary Examiner*—Tu B Hoang  
*Assistant Examiner*—Vinod D Patel  
(74) *Attorney, Agent, or Firm*—Oblon, Spivak, McClelland, Maier & Neustadt, P.C.

(57) ABSTRACT

A cleaning processing jig is inserted into a bolt heater hole, and pollution such as extraneous matter on an inner surface of the hole is removed by a waste cloth. A penetration processing jig is inserted into the hole, and the penetrant is made to uniformly penetrate into the inner surface by a sponge onto which a penetrant is applied. Then, a developing processing jig is inserted into the hole, and the inner surface is developed by injecting a developer toward the inner surface from an injection tip provided on a head. When a predetermined time elapses after the developing processing, a visual inspection tool in which a visible head is attached to a tip of a pipe is inserted into the hole, and the inner surface is visually inspected through a light pipe connected to the visible head.

10 Claims, 2 Drawing Sheets

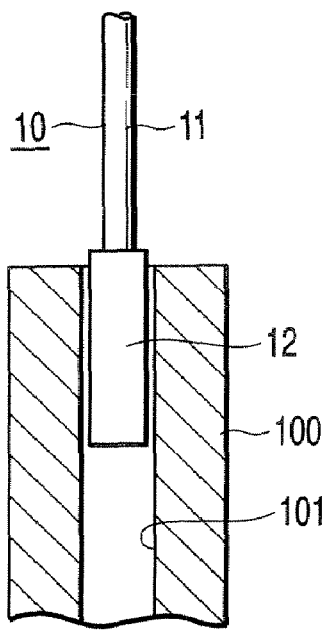
F I G. 1
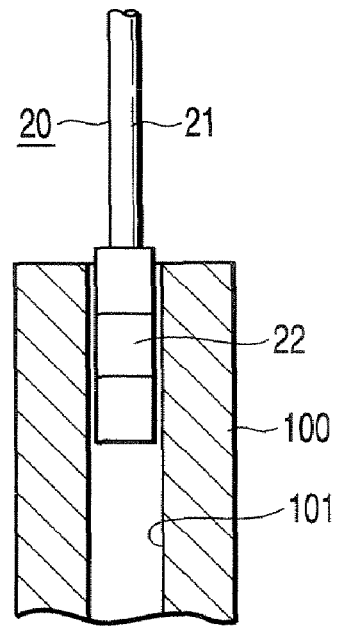
F I G. 2
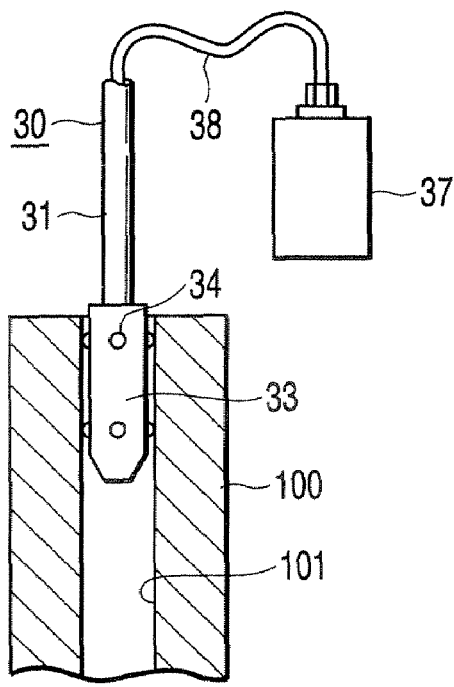
F I G. 3
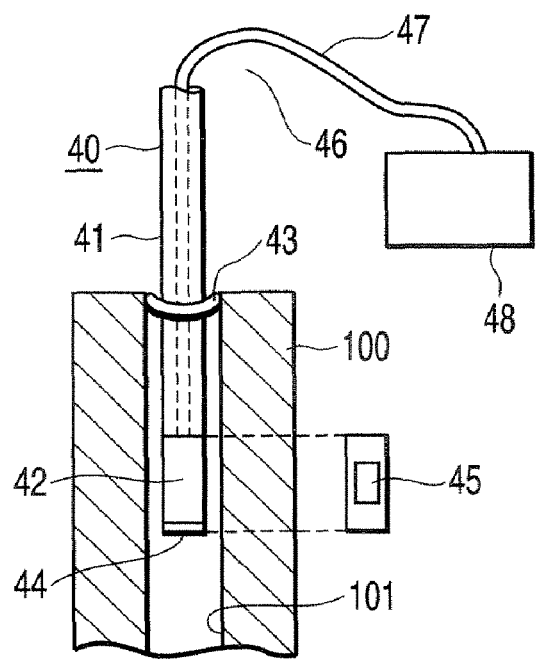
F I G. 4

METHOD FOR INSPECTING BOLT HEATER HOLE

CROSS-REFERENCE TO RELATED APPLICATIONS

This application is based upon and claims the benefit of priority from prior Japanese Patent Application No. 2006-032624, filed Feb. 9, 2006, the entire contents of which are incorporated herein by reference.

BACKGROUND OF THE INVENTION

1. Field of the Invention

The present invention relates to a method for inspecting a bolt heater hole provided for inspecting the soundness of a turbine casing clamping bolt.

2. Description of the Related Art

A hole (bolt heater hole) for heat-drawing the bolt in relation to a temperature at the time of driving a turbine is provided in a turbine casing clamping bolt, and a turbine casing is clamped in a state in which the bolt is heated to be a temperature substantially the same as the temperature at the time of driving the turbine by inserting a heater into the hole.

There is a risk that a crack or the like brought about in the bolt heater hole of such a turbine casing clamping bolt may result in breakage of the bolt. However, because an inspection of a bolt heater hole has not been conventionally required, an inspection technique thereof has not been particularly established.

For example, as a method for inspecting an inner surface of a tube body, a liquid penetrant test (for example, in Jpn. Pat. Appln. KOKAI Publication No. 09-196863) method has been known. In this liquid penetrant test method, a colored liquid or a fluorescent liquid which is generally strongly penetrative is applied onto a surface to be inspected. After the applied liquid is made to sufficiently penetrate into a defect plane of the surface, the penetrant on the surface is removed, the penetrant penetrated into the inner defect is sucked out with a white-micronized developer, and the surface is observed by being illuminated directly or by a black light.

However, when the above-described liquid penetrant test method is applied to an inspection of an inner surface of the bolt heater hole provided in the turbine casing clamping bolt described above, because the bolt heater hole is as small as 20 to 25 mmφ, and is made to be a bottomed and elongated hole, a large-scale device is required in order to automatically carry out a series of processings such as application of a penetrant onto the inner surface of the bolt heater hole, suction of the penetrant by a developer, and the like. Therefore, there is a problem that the structure thereof is complicated, which mounts the costs. Further, because the bolt heater hole has a limited length from the open end to the bottom face unlike a piping, even if an inspection jig is inserted into the bolt heater hole, the apical portion thereof is restricted by the bottom face of the bolt heater hole, making it difficult to apply the processing onto the entire area of the hole surface.

BRIEF SUMMARY OF THE INVENTION

The present invention has been achieved in consideration of the circumstances as described above, and an object of the invention is to provide a method for inspecting a bolt heater hole by which it is possible to easily carry out a liquid penetrant test onto an entire area of an inner surface of a holt heater hole provided in a turbine casing clamping bolt, with a simple structure and inexpensively.

In order to achieve the above-described object, there is provided a method for inspecting a bolt heater hole comprising: carrying out cleaning processing in which a cleaning processing jig in which a waste cloth is attached to a tip of a cleaning stick is inserted into a bolt heater hole provided in a turbine casing fixing bolt, and pollution such as extraneous matter and the like on an inner surface of the bolt heater hole is removed by the waste cloth while moving the cleaning stick straight; after the cleaning processing, carrying out penetration processing in which a penetration processing jig in which a sponge is attached to a tip of a penetration stick is inserted into the bolt heater hole after a penetrant is applied onto the sponge, and the penetrant is made to uniformly penetrate into the inner surface of the bolt heater hole by the sponge while moving the penetration stick straight; carrying out the cleaning processing when a predetermined time elapses after the penetrant has been uniformly applied to the inner surface of the bolt heater hole, and carrying out developing processing in which a developing processing jig, in which a head having an injection tip which injects a developer is fixed to a guide attached to a tip of a pipe, is inserted into the bolt heater hole, and the inner surface of the bolt heater hole is developed by injecting the developer guided into the guide through the pipe toward the inner surface of the bolt heater hole from the injection tip provided on the head while moving the pipe backward from a deeper portion; and when a predetermined time elapses after the developing processing, carrying out inspection processing in which a visual inspection tool in which a visible head is attached to a tip of a pipe is inserted into the bolt heater hole, and the inner surface of the bolt heater hole is visually inspected through a light pipe connected to the visible head while moving the pipe straight.

In accordance with the present invention, it is possible to easily carry out the liquid penetrant test onto the entire area of the inner surface of the bolt heater hole provided in the turbine casing clamping bolt, with a simple structure and inexpensively.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a cross-sectional view showing a state in which a cleaning processing jig used for a method for inspecting a bolt heater hole according to an embodiment of the present invention is inserted into a bolt heater hole;

FIG. 2 is a cross-sectional view showing a state in which a penetration processing jig is inserted into the bolt heater hole;

FIG. 3 is a cross-sectional view showing a state in which a developing processing jig is inserted into the bolt heater hole;

FIG. 4 is a cross-sectional view showing a state in which a visual inspection tool is inserted into the bolt heater hole.

DETAILED DESCRIPTION OF THE INVENTION

Figure 5:
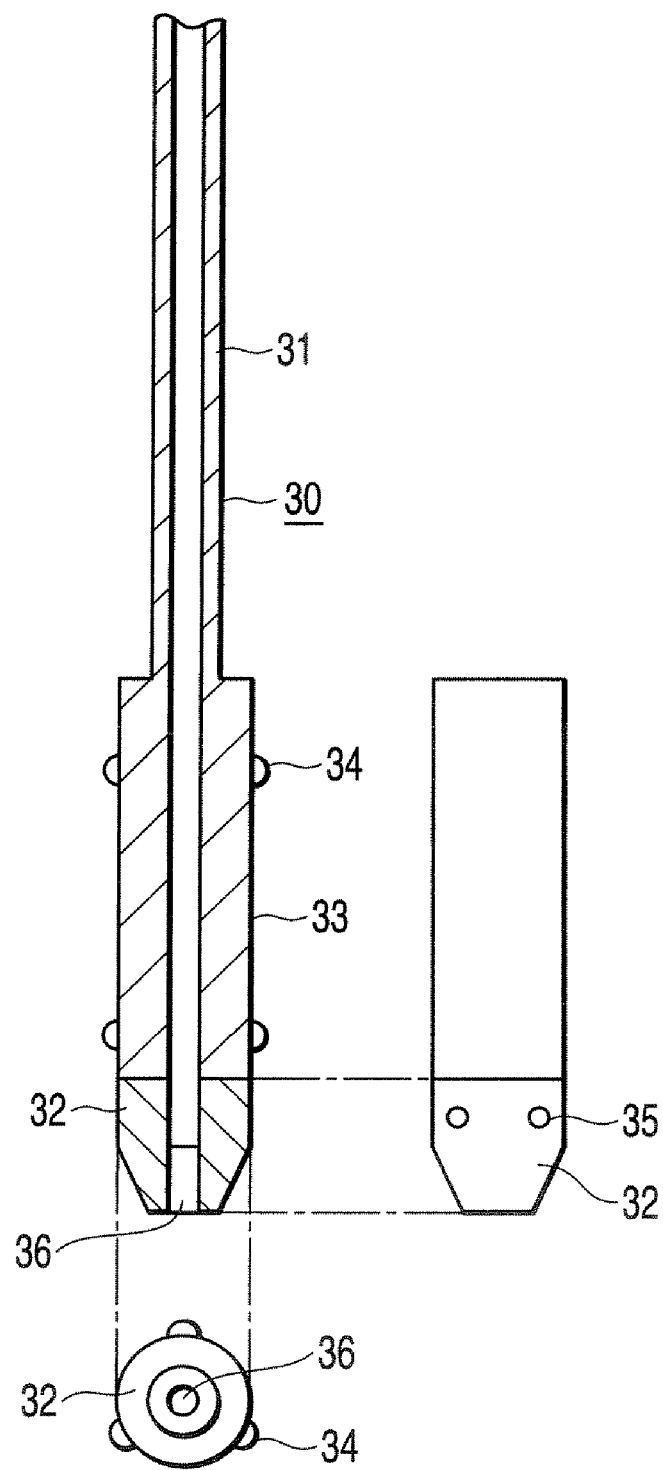
FIG. 5 is an explanatory view showing the developing processing jig shown in FIG. 3 in detail.

An embodiment of the present invention will be described hereinafter with reference to the drawings.

FIGS. 1 to 4 are diagrams showing a cleaning processing jig, a penetration processing jig, a developing processing jig, and a visual inspection tool, respectively, which are used for the embodiment of a method for inspecting a bolt heater hole according to the present invention.

With respect to a cleaning processing jig 10 shown in FIG. 1, a waste cloth (cleaning cloth) 12 is attached to the tip of a cleaning stick 11 having a diameter and a length which are determined in accordance with a diameter and a depth of a bolt heater hole 101 provided in a turbine casing clamping bolt 100.

With respect to a penetration processing jig 20 shown in FIG. 2, a sponge 22 which absorbs, for example, a red liquid which is strongly penetrative, is attached to the tip of a penetrating stick 21 having a diameter and a length which are determined in accordance with a diameter and a depth of the bolt heater hole 101 in the same way as in the above description.

With respect to a developing processing jig 30 shown in FIG. 3, a guide 33 is attached to the tip of a pipe 31 having a diameter and a length which are determined in accordance with a diameter and a depth of the bolt heater hole 101 in the same way as in the above description.

In the above-described guide 33, at least three center supporting pins 34 which are extensible radially are provided at even intervals (at intervals of 120°) in a circumferential direction at the same level of the peripheral surface as shown in FIG. 5. These three center supporting pins 34 contact the inner surface of the bolt heater hole 101 to support the developing processing jig 30 so as to always bring its own central axis line on the central line of the bolt heater hole 101. Further, a head 32 having an injection tip 36 injecting a developer is fixed to the apical portion of the guide 33 by clamping bolts 35.

Then, a tube 38 through which a developer is guided from a spray can 37 into the head 32 is inserted on the central axis line of the pipe 31 and the guide 33.

With respect to the visual inspection tool 40 shown in FIG. 4, a visible head 42 is attached to the tip of a pipe 41 having a diameter and a length which are determined in accordance with a diameter and a depth of the bolt heater hole 101 in the same way as in the above description.

At least three center supporting rings 43, which contact the inner surface of the bolt heater hole 101 to support the visual inspection tool 40 so as to always bring the central axis line of the visible head 42 on the central line of the bolt heater hole 101, are fixed at the outer circumference of the pipe 41 at even intervals. Further, a direct-viewing lens 44 is provided to the apical surface of the visible head 42, and it is possible to use a side-viewing lens 45 as needed.

On the other hand, reference numeral 46 is a fiber scope, and a light pipe 47 of the fiber scope 46 is connected to the pipe visible head 42 through the pipe 41 of the visual inspection tool 41, which makes it possible to visually inspect the inner surface of the bolt heater hole 101 on a monitor 48 provided outside.

Next, a method for inspecting the inner surface of the bolt heater hole by using the respective jigs with structures as described above will be described.

First, as a pretreatment (cleaning processing), pollution such as extraneous matter and the like on the inner surface of the bolt heater hole 101 provided in the bolt 100 is removed by using the cleaning processing jig 10 shown in FIG. 1. This is carried out such that the cleaning stick 11 is inserted into the bolt heater hole 101 while rotating the cleaning stick 11, and the waste cloth 12 attached to the tip wipes the inner surface of the bolt heater hole 101. As a cleaning solvent, for example, one consisting primarily of heptane, butane, or the like is used.

Next, a penetrant is made to penetrate into the inner surface of the bolt heater hole 101 by using the penetration processing jig 20 shown in FIG. 2. Concretely, a strong penetrative penetrant colored, for example, in red is applied onto the sponge 22 attached to the tip of the penetration stick 21, and the penetrant is made to uniformly penetrate into the inner surface of the bolt heater hole 101. As a penetrant, for example, one consisting primarily of hydrocarbon oil, plastic solvent, glycol ethel, or the like is used.

Then, when a predetermined penetration time elapses after the penetrant has been applied uniformly onto the inner surface of the bolt heater hole 101, cleaning is again carried out in the same way as in the above description such that the waste cloth 12 attached to the tip of the cleaning stick 11 wipes the inner surface of the bolt heater hole 101 by using the cleaning processing jig 10 shown in FIG. 1. In this case, because the waste cloth 12 is polluted due to the previous cleaning, this is exchanged with a new waste cloth 12 at the time of cleaning after the application of the penetrant.

After such penetration processing and cleaning processing are repeatedly carried out several times (4 to 5 times), developing processing is carried out by using the developing processing jig 30 shown in FIG. 3. Namely, when the guide 33 attached to the tip of the pipe 31 is inserted into the bolt heater hole 101, the three center supporting pins 34 provided at even intervals at the same level of the peripheral surface contact the inner surface of the bolt heater hole 101, and the developing processing jig 30 is supported so as to always bring its own central axis line on the central line of the bolt heater hole 101.

In this state, when, for example, a white developer is guided into the guide 33 attached to the tip of the pipe 31 via the tube 38 from the spray can 37, this developer is injected toward the inner surface of the bolt heater hole 101 from the injection tip 36 provided to the head 32. Then, by sequentially moving the developing processing jig 30 toward the shallower portion of the bolt heater hole 101, the developer is sprayed uniformly onto the inner surface of the bolt heater hole 101. As a developer, for example, one consisting primarily of butane, propane, alcohol, aliphatic hydrocarbon, silica, and the like is used.

Next, when a predetermined developing time elapses after the developer is sprayed onto the inner surface of the bolt heater hole 101, an inspection of the bolt heater hole 101 is started by using the visual inspection tool shown in FIG. 4.

Namely, at the time of inserting the pipe 41 into the bolt heater hole 101, the visual inspection tool 40 is supported so as to bring the central axis line of the visible head 42 on the central line of the bolt heater hole 101 by adjusting screw-in positions of acryl bolts which fix the center supporting rings 43.

In this state, the light pipe 47 of the fiber scope 46 is inserted into the pipe visible head 42 through the pipe 41, and the front of the bolt heater hole 101 is viewed directly by the direct-viewing lens 44 provided on the apical surface of the visible head 42 while moving the pipe 41 toward the deeper portion of the bolt heater hole 101. When a crack or the like is found, the extent, the proceeding, and the like of the crack are visually inspected on the monitor 48 of the fiber scope 46 by the side-viewing lens 45 by moving the visible head 42.

When the inspection is terminated in this way, as a post-treatment, cleaning is carried out such that the bolt heater hole 101 is immersed in a cleaning solvent to be clean after the developer is removed by using the cleaning processing jig 10 shown in FIG. 1.

In this way, in accordance with the present embodiment, after the cleaning processing, the penetration processing, and the developing processing are carried out by respectively using the cleaning processing jig 10, the penetration processing jig 20, and the developing processing jig 30, it is possible to easily confirm whether or not a crack or the like is brought about in the inner surface of the bolt heater hole 101 by an visual inspection by using the visual inspection tool and the fiber scope 46.

Here, the cleaning processing jig 10 is structured such that the waste cloth 12 is attached to the tip of the cleaning stick 11 having a diameter and a length which are determined in accordance with a diameter and a depth of the bolt heater hole 101. Therefore, it is possible to effectively wash the inner surface of the elongated and bottomed bolt heater hole 101.

Further, the penetration processing jig 20 is structured such that the sponge 22 which absorbs a penetrant is attached to the tip of the penetration stick 21 having a diameter and a length which are determined in accordance with a diameter and a depth of the bolt heater hole 101. Therefore, it is possible to uniformly apply the penetrant onto the inner surface of the elongated and bottomed bolt heater hole 101.

Moreover, the developing processing jig 30 is structured such that the guide 33 is attached to the tip of the pipe 31 having a diameter and a length which are determined in accordance with a diameter and a depth of the bolt heater hole 101, and the three center supporting pins 34 which are extensible radially are provided at even intervals at the same level of the peripheral surface of the guide 33. Therefore, it is possible to support the developing processing jig 30 so as to always bring its own central axis line on the central line of the bolt heater hole 101. Further, the developing processing jig 30 is structured such that the head 32 in a state in which the injection tip 36 is positioned on the center thereof is fixed to the apical portion of the guide 33 by the clamping bolts 35. Therefore, it is possible to spray a developer so as to be remote axially and uniform with respect to the elongated and bottomed bolt heater hole 101, and it is possible to uniformly apply the developer onto the inner surface of the bolt heater hole 101, enabling satisfactory developing processing.

On the other hand, the visual inspection tool is structured such that the visible head 42 is attached to the tip of the pipe 41 having a diameter and a length which are determined in accordance with a diameter and a depth of the bolt heater hole 101, and further, is fixed so as to have even intervals from the three center supporting rings 43 at the peripheral surface of the pipe 41. Therefore, it is possible to always bring the central axis line of the visible head 42 on the central line of the bolt heater hole 101. Further, the front of the bolt heater hole 101 is viewed directly by the direct-viewing lens 44 provided on the apical surface of the visible head 42, and the extent, the proceeding, and the like of a clack or the like can be visually inspected by the side-viewing lens 45 and the fiber scope.

Note that, in the above-described embodiment, a case in which the inner surface of the bolt heater hole 101 is inspected by the fiber scope 46 by using the visual inspection tool 40 has been described. However, this may be inspected by an image scope.

Further, the developing processing jig 30 and the visual inspection tool 40 can be used for a case in which a diameter of a bolt heater hole is varied. Namely, the developing processing jig 30 can cope with a bolt heater hole with a different hole diameter by adjusting by the three center supporting pins 34 which are extensible radially provided at even intervals at the same level of the peripheral surface of the guide 33. Further, the visual inspection tool 40 can cope with a bolt heater hole with a different hole diameter by adjusting by fixing the three center supporting rings 43 to the peripheral surface of the pipe 41.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for inspecting a bolt heater hole comprising:
    carrying out cleaning processing in which a cleaning processing jig in which a waste cloth is attached to a tip of a cleaning stick, is inserted into a bolt heater hole provided in a turbine casing fixing bolt, and pollution such as extraneous matter on an inner surface of the bolt heater hole is removed by the waste cloth while moving the cleaning stick straight;
    after the cleaning processing, carrying out penetration processing in which a penetration processing jig in which a sponge is attached to a tip of a penetration stick, is inserted into the bolt heater hole after a penetrant is applied onto the sponge, and the penetrant is made to uniformly penetrate into the inner surface of the bolt heater hole by the sponge while moving the penetration stick straight;
    carrying out the cleaning processing when a predetermined time elapses after the penetrant has been uniformly applied to the inner surface of the bolt heater hole, and carrying out developing processing in which a developing processing jig, in which a head having an injection tip which injects a developer is fixed to a guide attached to a tip of a pipe, is inserted into the bolt heater hole, and the inner surface of the bolt heater hole is developed by injecting the developer guided into the guide through the pipe toward the inner surface of the bolt heater hole from the injection tip provided on the head while moving the pipe backward from a deeper portion; and
    when a predetermined time elapses after the developing processing, carrying out inspection processing in which a visual inspection tool in which a visible head is attached to a tip of a pipe is inserted into the bolt heater hole, and the inner surface of the bolt heater hole is visually inspected through a light pipe connected to the visible head while moving the pipe straight,
    wherein at least three center supporting pins which are extensible radially are provided at even intervals in a circumferential direction at an peripheral surface of the guide of the developing processing jig, and the developing processing jig is supported by the supporting pins so as to bring a central axis line of the visible head on a central line of the bolt heater hole.

2. The method for inspecting a bolt heater hole according to claim 1, wherein
    after cleaning processing is carried out as a pretreatment, the cleaning processing and the penetration processing are repeatedly carried out several times after a passage of a predetermined time from the penetration processing.

3. The method for inspecting a bolt heater hole according to claim 1, wherein
when the inspection processing is terminated, the developer is removed by using the cleaning processing jig as a posttreatment, after which cleaning of the inner surface of the bolt heater hole is carried out by being immersed in a cleaning solvent.

4. The method for inspecting a bolt heater hole according to claim 1, wherein
a direct-viewing lens is provided on an apical surface of the visible head of the visual inspection tool, a side-viewing lens is provided at a side surface near thereto, a crack is detected by directly viewing a front of the bolt heater hole by the direct-viewing lens, and an extent and a proceeding of the detected crack are detected by the side-viewing lens.

5. The method for inspecting a bolt heater hole according to claim 1, wherein
the visual inspection of the bolt heater hole is carried out by a fiber scope or an image scope in which a light pipe is connected to the visible head.

6. A method for inspecting a bolt heater hole comprising:
carrying out cleaning processing in which a cleaning processing jig in which a waste cloth is attached to a tip of a cleaning stick1 is inserted into a bolt heater hole provided in a turbine casing fixing bolt, and pollution such as extraneous matter on an inner surface of the bolt heater hole is removed by the waste cloth while moving the cleaning stick straight;

after the cleaning processing, carrying out penetration processing in which a penetration processing jig in which a sponge is attached to a tip of a penetration stick, is inserted into the bolt heater hole after a penetrant is applied onto the sponge, and the penetrant is made to uniformly penetrate into the inner surface of the bolt heater hole by the sponge while moving the penetration stick straight;

carrying out the cleaning processing when a predetermined time elapses after the penetrant has been uniformly applied to the inner surface of the bolt heater hole, and carrying out developing processing in which a developing processing jig, in which a head having an injection tip which injects a developer is fixed to a guide attached to a tip of a pipe, is inserted into the bolt heater hole, and the inner surface of the bolt heater hole is developed by injecting the developer guided into the guide through the pipe toward the inner surface of the bolt heater hole from the injection tip provided on the head while moving the pipe backward from a deeper portion; and when a predetermined time elapses after the developing processing, carrying out inspection processing in which a visual inspection tool in which a visible head is attached to a tip of a pipe is inserted into the bolt heater hole, and the inner surface of the bolt heater hole is visually inspected through a light pipe connected to the visible head while moving the pipe straight, wherein center supporting rings are provided at an peripheral surface of the pipe of the visual inspection tool, and the visual inspection tool is fixed by the center supporting rings so as to bring a central axis line of the visible head on a central line of the bolt heater hole.

7. The method for inspecting a bolt heater hole according to claim 6, wherein
after cleaning processing is carried out as a pretreatment, the cleaning processing and the penetration processing are repeatedly carried out several times after a passage of a predetermined time from the penetration processing.

8. The method for inspecting a bolt heater hole according to claim 6, wherein
when the inspection processing is terminated, the developer is removed by using the cleaning processing jig as a posttreatment, after which cleaning of the inner surface of the bolt heater hole is carried out by being immersed in a cleaning solvent.

9. The method for inspecting a bolt heater hole according to claim 6, wherein
a direct-viewing lens is provided on an apical surface of the visible head of the visual inspection tool, a side-viewing lens is provided at a side surface near thereto, a crack is detected by directly viewing a front of the bolt heater hole by the direct-viewing lens, and an extent and a proceeding of the detected crack are detected by the side-viewing lens.

10. The method for inspecting a bolt heater hole according to claim 6, wherein
the visual inspection of the bolt heater hole is carried out by a fiber scope or an image scope in which a light pipe is connected to the visible head.

* * * * *